US011147488B2

(12) United States Patent
Lee et al.

(10) Patent No.: US 11,147,488 B2
(45) Date of Patent: Oct. 19, 2021

(54) ELECTRONIC DEVICE AND CONTROLLING METHOD THEREOF

(71) Applicants: Hyundai Motor Company, Seoul (KR); Kia Motors Corporation, Seoul (KR)

(72) Inventors: Jia Lee, Seoul (KR); Seok-young Youn, Seoul (KR); Jimin Han, Gyeonggi-do (KR); Kye Yoon Kim, Gyeonggi-do (KR); Seunghyun Woo, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 112 days.

(21) Appl. No.: 16/683,362

(22) Filed: Nov. 14, 2019

(65) Prior Publication Data

US 2020/0261008 A1 Aug. 20, 2020

(30) Foreign Application Priority Data

Feb. 19, 2019 (KR) ........................ 10-2019-0019498

(51) Int. Cl.
  *A61B 5/16* (2006.01)
  *A61B 5/00* (2006.01)
  *A61B 5/01* (2006.01)
(52) U.S. Cl.
  CPC ................ *A61B 5/165* (2013.01); *A61B 5/01* (2013.01); *A61B 5/486* (2013.01)

(58) Field of Classification Search
  CPC ........... A61B 5/165; A61B 5/486; A61B 5/01; A61B 5/6832; A61B 5/7445; A61B 5/742; A61B 5/18
  See application file for complete search history.

(56) References Cited

U.S. PATENT DOCUMENTS

| | | | |
|---|---|---|---|
| 4,220,016 A * | 9/1980 | Frenger .............. | A44C 15/0005 63/14.9 |
| 9,064,390 B1 * | 6/2015 | Clark ........................ | G08B 5/36 |
| 2003/0139654 A1 * | 7/2003 | Kim ................... | A61B 5/02405 600/300 |
| 2005/0283055 A1 * | 12/2005 | Shirai ...................... | A61B 5/16 600/301 |
| 2016/0070245 A1 * | 3/2016 | Lee ...................... | A61B 5/0004 700/49 |
| 2016/0198996 A1 * | 7/2016 | Dullen ................. | A61B 5/6832 600/301 |
| 2017/0105662 A1 * | 4/2017 | Silawan ................. | A61B 5/021 |

(Continued)

*Primary Examiner* — Jennifer Pitrak McDonald
*Assistant Examiner* — Michael T. Holtzclaw
(74) *Attorney, Agent, or Firm* — Mintz Levin Cohn Ferris Glovsky and Popeo, P.C.; Peter F. Corless

(57) ABSTRACT

An electronic device attached to a user's skin is provided to determine a user emotion based on measured bio-signals. An image corresponding to the determined emotion is displayed. The electronic device includes a skin-attachment apparatus having a bonding unit for bonding to a user's skin and a bio-signal sensor that measures the bio-signals of the user. A display unit and a controller are connected with the skin-attachment apparatus. The controller determines the user emotion based on the bio-signals acquired from the bio-signal sensor and operates the display unit to display at least one of a color and a pattern corresponding to the determined emotion.

18 Claims, 12 Drawing Sheets

(56) References Cited

U.S. PATENT DOCUMENTS

2018/0032126 A1* 2/2018 Liu .................... G06K 9/00302
2018/0211102 A1* 7/2018 Alsmadi ............ G06K 9/00228
2018/0303397 A1* 10/2018 Krupat ................ A61B 5/0077

* cited by examiner

| BIO-SIGNAL | EMOTION FACTOR | | | | | | | | | | | | | | | | |
|---|---|---|---|---|---|---|---|---|---|---|---|---|---|---|---|---|---|
| | Disgust | Anger | Fear | Anxiety | Sadness | Stress | Frustration | Boredom | Neutral | Interest | Distress | Platonic Love | Romantic Love | Pleasure | Joy |
| GSR | .875 | .775 | .653 | .353 | .545 | | | | .655 | .545 | | | | | .353 |
| EEG | .555 | 0.864 | .878 | | .545 | | .464 | .477 | .577 | | | | .353 | | |

| EXPRESSION | Disgust | Anger | Fear | Anxiety | Sadness | Stress | Frustration | Boredom | Neutral | Interest | Distress | Platonic Love | Romantic Love | Pleasure | Joy |
|---|---|---|---|---|---|---|---|---|---|---|---|---|---|---|---|
| EXPRESSION 1 | .65 | .87 | .35 | .88 | .14 | | | | .63 | .53 | | | | | .33 |
| EXPRESSION 2 | .01 | 0.09 | .11 | | .54 | | .31 | .51 | .61 | | | | | | .97 |
| EXPRESSION 3 | .70 | | .90 | | .19 | .87 | | | | | | | | | |

FIG. 7

| DISPLAY / EMOTION | COLOR | PATTERN |
|---|---|---|
| DEPRESSION | BLUE | RAINFALL PATTERN/ DEPRESSED EXPRESSION |
| HAPPINESS | PINK | FLOWER PATTERN/ HAPPY EXPRESSION |

FIG. 10

| EMOTION OF OBJECT | FEEDBACK EMOTION |
|---|---|
| ANGER | SORRY |
| HAPPINESS | HAPPINESS |

ELECTRONIC DEVICE AND CONTROLLING METHOD THEREOF

CROSS-REFERENCE TO RELATED APPLICATION(S)

This application is based on and claims priority under 35 U.S.C. § 119 to Korean Patent Application No. 10-2019-0019498, filed on Feb. 19, 2019, the disclosure of which is incorporated by reference in its entirety.

BACKGROUND

1. Technical Field

The present disclosure relates to an electronic device attached to a user and that outputs an image, and a control method thereof, and more particularly, to an electronic device and method for determining a user emotion based on measured bio-signals and displaying an image related thereto.

2. Description of the Related Art

Recently, miniaturized electronic devices such as wearable devices worn by users are being actively developed. In particular, development of skin electronics, which are electronic devices capable of attaching to a user's skin, has been actively carried out. Such skin electronic devices are attached to the user's skin to measure the user's biological signals, or a specific image may be output.

SUMMARY

The present disclosure provides an electronic device attached to a user's skin to determine the user's emotion based on measured bio-signals, and displays an image corresponding to the determined emotion, and method thereof.

In accordance with an aspect of the present disclosure, an electronic device may include a skin-attachment apparatus configured to include a bonding unit for bonding to a user's skin, a bio-signal sensor configured to measure bio-signals of the user, and a display unit; and a controller configured to be connected with the skin-attachment apparatus, determine the user's emotion based on the bio-signals acquired from the bio-signal sensor, and operate the display unit to display at least one of a color and a pattern corresponding to the determined emotion.

The display unit may include a heating circuit; and a thermochromic pigment layer configured to include at least one thermochromic pigment provided on the heating circuit. The controller may be configured to determine the color that corresponds to the determined emotion, and operate the heating circuit to generate heat at a temperature that corresponds to the determined color. The controller may then be configured to determine the pattern that corresponds to the determined emotion, and operate the heating circuit to generate heat at a region that corresponds to the determined pattern.

Additionally, the controller may be configured to determine a facial expression that corresponds to the determined emotion, determine a pattern for each body part based on the feature of the body part in the determined facial expression, and operate the display unit to display the pattern among the determined patterns that correspond to the body part to which the skin-attachment apparatus is attached.

The skin-attachment apparatus, respectively provided in plural, may be attached to the different body parts. The electronic device may further include a camera configured to acquire image data of the user's surroundings. The controller may be configured to determine at least one of a facial expression and an action of an object based on image data of the object included in the image data and determine an emotion of the object based on at least one of the determined facial expression and the action.

The controller may be configured to determine a feedback emotion that corresponds to the emotion of the object, and operate the display unit to display at least one of the color and the pattern that corresponds to the determined feedback emotion. The controller may be configured to perform an arithmetic operation on the emotion of the object using a neural network and determine the feedback emotion that corresponds to the emotion of the object based on the information on the operation performed using the neural network. The controller may also be configured to determine a change in the emotion of the object with respect to at least one of the color and the pattern corresponding to the determined feedback emotion based on the image data of the object and may then be configured to update the neural network.

In accordance with an aspect of the present disclosure, a method for controlling an electronic device that includes a skin-attachment apparatus bonded to a user's skin, a bio-signal sensor configured to bio-signals of the user, and a display unit, the method including determining the user's emotion based on the bio-signals acquired from the bio-signal sensor; and operating the display unit to display at least one of a color and a pattern that corresponds to the determined emotion.

The display unit may include a heating circuit; and a thermochromic pigment layer configured to include at least one thermochromic pigment provided on the heating circuit. The operating of the display unit may include determining the color corresponding to the determined emotion; and operating the heating circuit to generate heat at a temperature corresponding to the determined color. In addition, the operating of the display unit may include determining the pattern corresponding to the determined emotion; and operating the heating circuit to generate heat at a region corresponding to the determined pattern.

The operating of the display unit may further include determining a facial expression corresponding to the determined emotion; and determining the pattern for each body part based on the feature of the body part in the determined facial expression; and operating the display unit to display the pattern among the determined patterns corresponding to the body part to which the skin-attachment apparatus is attached. The skin-attachment apparatus, respectively provided in plural, may be attached to different body parts. The electronic device may further include a camera configured to acquire image data of the user's surroundings.

The method may further include determining at least one of a facial expression and an action of an object based on image data of the object included in the image data; and determining an emotion of the object based on at least one of the determined facial expression and the action. In addition, the method may include: determining a feedback emotion that corresponds to the emotion of the object; and operating the display unit to display at least one of the color and the pattern corresponding to the determined feedback emotion.

The determining of the feedback emotion may include performing an arithmetic operation on the emotion of the object using a neural network; and determining the feedback emotion that corresponds to the emotion of the object based on the information on the operation performed using the neural network. The method may further include determining a change in the emotion of the object with respect to at least one of the color and the pattern corresponding to the determined feedback emotion based on the image data of the object; and updating the neural network based on the determined feedback emotion and the emotion change of the object.

BRIEF DESCRIPTION OF THE DRAWINGS

These and/or other aspects of the invention will become apparent and more readily appreciated from the following description of the exemplary embodiments, taken in conjunction with the accompanying drawings of which:

FIG. 7 is a diagram illustrating information on colors and patterns corresponding to an emotion according to an exemplary embodiment;

FIG. 10 is a diagram illustrating information on a feedback emotion corresponding to an emotion of an object according to an exemplary embodiment;

DETAILED DESCRIPTION

Figure 1:
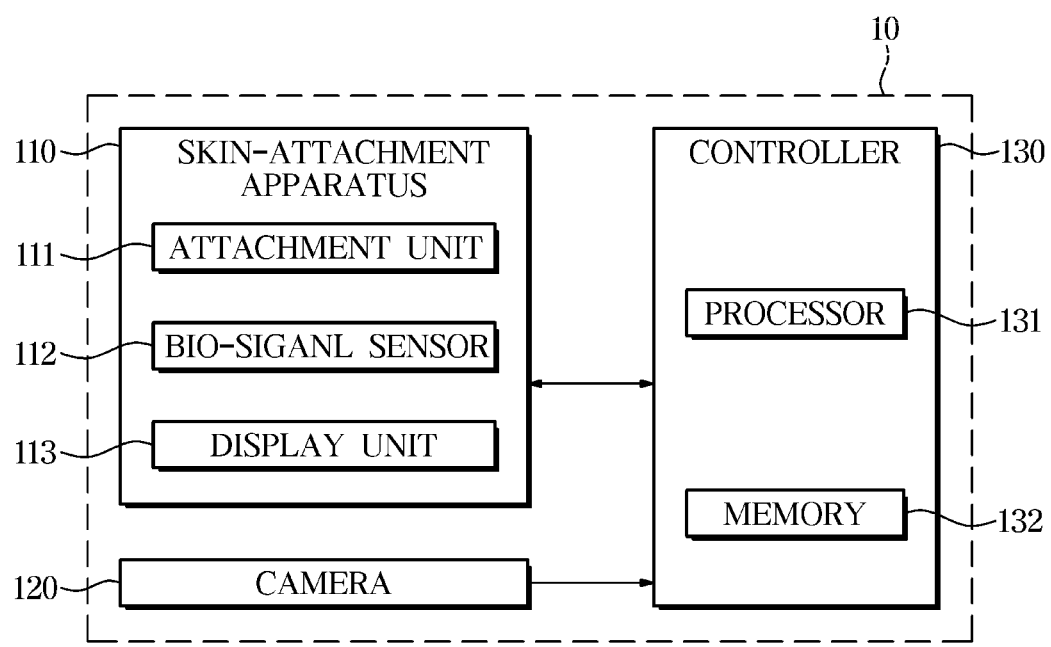
FIG. 1 is a block diagram of an electronic device according to an exemplary embodiment.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Reference will now be made in detail to the exemplary embodiments of the present disclosure, examples of which are illustrated in the accompanying drawings, wherein like reference numerals refer to like elements throughout. This specification does not describe all elements of the exemplary embodiments of the present disclosure and detailed descriptions on what are well known in the art or redundant descriptions on substantially the same configurations may be omitted.

Throughout the specification, when an element is referred to as being "connected to" another element, it may be directly or indirectly connected to the other element and the "indirectly connected to" includes being connected to the other element via a wireless communication network. The terms 'unit, module, member, and block' used herein may be implemented using a software or hardware component. According to an embodiment, a plurality of 'units, modules, members, or blocks' may also be implemented using an element and one 'unit, module, member, or block' may include a plurality of elements. The reference numerals used in operations are used for descriptive convenience and are not intended to describe the order of operations and the operations may be performed in a different order unless otherwise stated.

Hereinafter, embodiments of the present disclosure will be described in detail with reference to the accompanying drawings. FIG. 1 is a block diagram of an electronic device according to an exemplary embodiment, FIG. 2 is an external view of an electronic device according to an embodiment, and FIG. 3 is an exploded view of a display unit according to an exemplary embodiment.

Referring to FIG. 1, an electronic device 10 according to an exemplary embodiment may include a skin-attachment apparatus 110 attached to a user's skin to measure the user's biological signals and output an image, and a controller 130 configured to operate the skin-attachment apparatus 110 to determine the user's emotion based on a camera 120 and the bio-signals, and to output the image that corresponds to the determined emotion.

Figure 2:
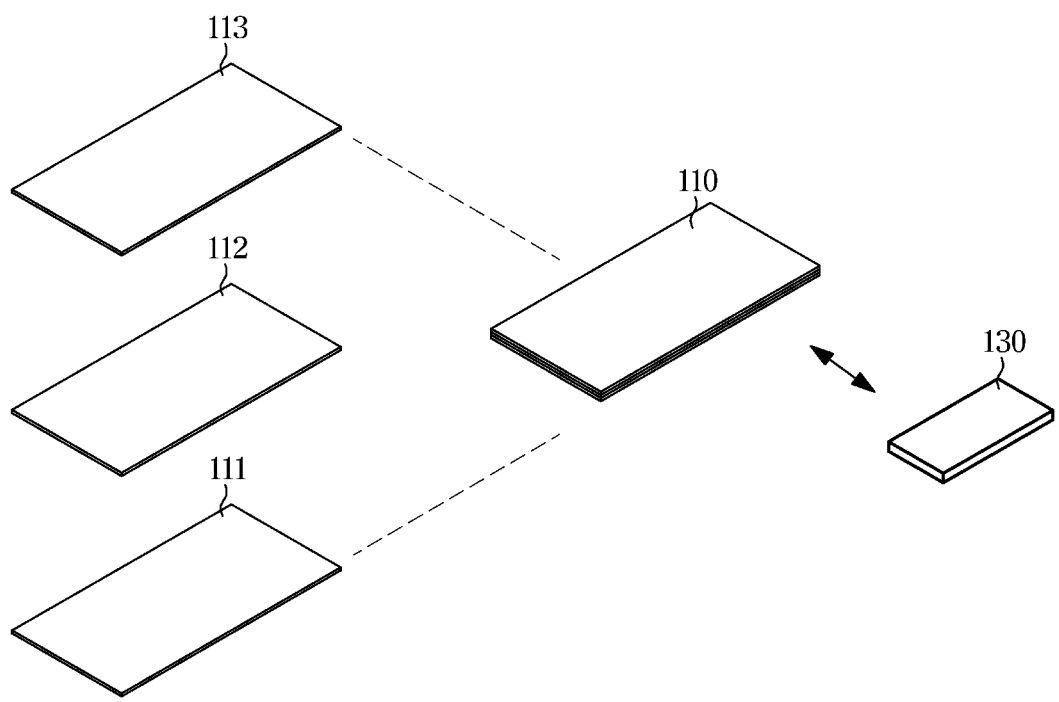
FIG. 2 is an external view of an electronic device according to an exemplary embodiment.
Figure 3:
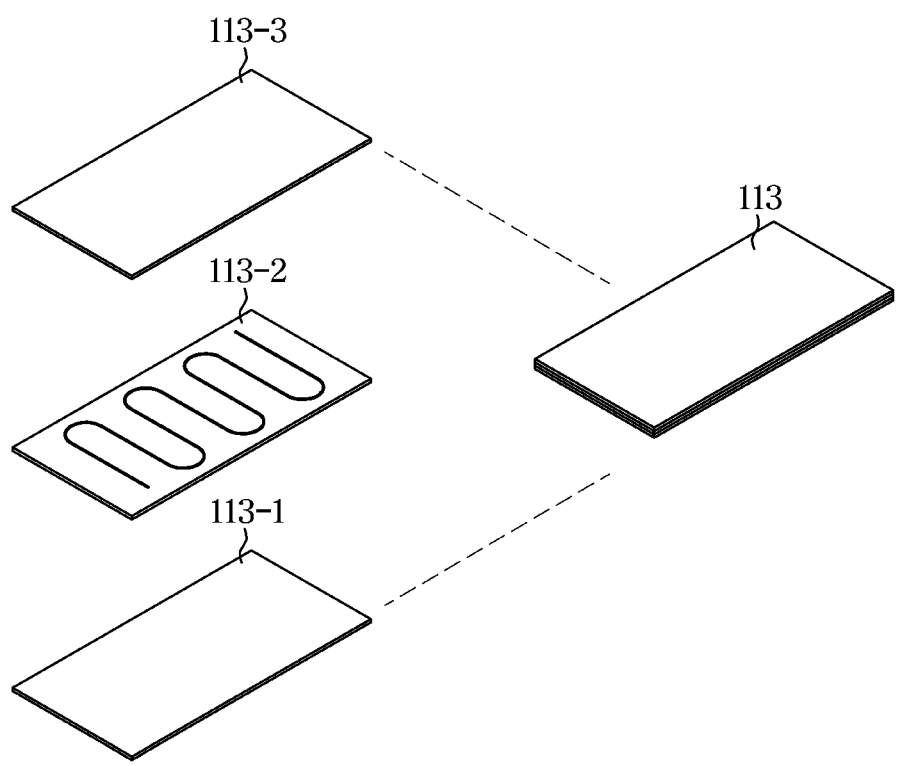
FIG. 3 is an exploded view of a display unit according to an exemplary embodiment.

Referring to FIG. 2, the electronic device 10 according to one exemplary embodiment may include the skin-attachment apparatus 110 and the controller 130 as separate modules. Specifically, the skin-attachment apparatus 110 may be provided with at least one apparatus and may be attached to the skin (e.g., bonded by adhesive or similar removable material). In addition, the controller 130 may be included in a component separate from the skin-attachment apparatus 110, and may be provided in a wearable device. For example, the main body of the controller 130 may be provided in the form of a hair clip worn on the user's head, in the form of glasses, or other similar type of wearable feature.

In other words, the controller 130 may correspond to a type of control device, and may include a processor 131 for collecting and processing information received from the skin-attachment apparatus 110, various types of information necessary for processing of the processor 131, and a memory 132 for storing the results. At this time, the controller 130 may be configured to perform wire communication or wireless communication with at least one of the skin-attachment apparatuses 110 via the communication module, thereby transmitting/receiving data to/from each other.

Accordingly, the skin-attachment apparatus 110 and the controller 130 may further include a communication module in addition to the configuration shown in FIG. 1. The communication module included in the skin-attachment apparatus 110 may be provided in the form of a film. The communication module may include, for wireless communication, a cellular module, a WiFi module, a Bluetooth module, a GNSS module, an NFC module, and an RF module. In addition, the communication modules of the skin-attachment apparatus 110 and the controller 130 may be connected via a communication cable for wired communication.

As shown in FIGS. 1 and 2, the skin-attachment apparatus 110 according to one exemplary embodiment may include an attachment unit 111 attached to the user's skin, a bio-signal sensor 112 configured to measure bio-signals of the user, and a display unit 113 configured to output an image under the operation of the controller 130. The attachment unit 111, the bio-signal sensor 112, and the display unit 113 may each be provided in a film form and may be included in the skin-attachment apparatus 110 to form a layer therebetween.

Specifically, the skin-attachment apparatus 110 may include a layer including the attachment unit 111, a layer including the bio-signal sensor 112 provided on the layer including the attachment unit 111, and a layer including the display unit provided on the layer including the bio-signal sensor 112. The attachment unit 111 according to one exemplary embodiment may include an adhesive material that directly contacts the user's skin and attaches to the user's skin. In other words, the attachment unit 111 may correspond to an adhesive film that may be attached to and detached from the user's skin. For example, the attachment unit 111 may correspond to a silk conductive adhesive film using a silk polymer. However, the attachment unit 111 is not limited to the above example, and may be included in the attachment unit 111 as long as it is an adhesive film composed of a material detachable to the user's skin.

The bio-signal sensor 112 according to an exemplary embodiment may include at least one of a galvanic skin response (GSR) sensor configured to measure the electrical conductivity of the skin that varies based on the amount of perspiration of the user, a skin temperature sensor, a heart rate (HR) sensor configured to measure the user's heart rate, an electroencephalogram (EEG) sensor configured to measure the user's brain waves, a speech recognition sensor configured to measure the user's voice signal, and a blood pressure measuring sensor configured to measure a blood pressure. At this time, the bio-signal sensor 112 may be included in another layer stacked on the layer including the attachment unit 111, and may be provided in the form of a film. In addition, the sensors included in the bio-signal sensor 112 are not limited to the above sensors, and sensors capable of measuring or collecting human bio-signals may be included without limitation.

The display unit 113 according to one exemplary embodiment may be included in another layer stacked on the layer including the bio-signal sensor 112, and may be provided in the form of a film. In other words, the display unit 113 may correspond to a skin display that may be attached to the skin. The display unit 113 may further include a processor and a memory for outputting an intended image by controlling the configuration of the display unit 113 under the operation of the controller 130.

The display unit 113 according to one exemplary embodiment may include a plurality of light emitting diodes (LEDs), and the plurality of LEDs may be arranged to form an array. The LEDs may correspond to, for example, a micro LED, and the LED array may be embedded on a thin rubber sheet forming a layer comprising the display unit 113. In particular, the display unit 113 may be configured to display various colors including R (red) light emitting elements, G (green) light emitting elements, and B (blue) light emitting elements.

In addition, the display unit 113 may include an insulating layer 113-1, a heat generating circuit 113-2, and a thermochromic pigment layer 113-3 as shown in FIG. 3. In other words, the display unit 113 may include the insulating layer 113-1, a layer including the heat generating circuit 113-2 stacked on the insulating layer 113-1, and the thermochromic pigment layer 113-3 stacked on the layer including the heat generating circuit 113-2. The insulating layer 113-1 prevents the heat output from the heat generating circuit 113-2 from being transmitted to the bio-signal sensor 112 and the attachment unit 111, and ultimately, prevents heat being transmitted to the skin of the user. Accordingly, the insulating layer 113-1 may include an insulating material.

The heat generating circuit 113-2 may be configured to generate heat at various temperatures according to the current flowing under the operation of the controller 130 and may be configured to generate heat at different temperatures based on positions on the heat generating circuit 113-2. Accordingly, the heat generating circuit 113-2 may include a plurality of circuits which are mutually opened for each position. In addition, the thermochromic pigment layer 113-3 may include a thermochromic pigment having a different color based on the temperature. The thermochromic pigment layer 113-3 may include at least one thermochromic pigment having a different reference temperature, and may be changed into various colors based on the temperature. In other words, the thermochromic pigment layer 113-3 may display various colors and patterns based on the temperature change of the heat generating circuit 113-2.

Further, the thermochromic pigment may include microcapsules with color that changes based on the reference temperature, and has reversibility. Specifically, the microcapsules contain a solid solvent, and two substances exhibiting color are bonded on the solid solvent. When the temperature increases, the solid solvent on the microcapsule melts and becomes a liquid solvent, in which case the two color-coded materials may be separated and exhibit different colors. Further, when the temperature decreases to less than the reference temperature, the liquid solvent on the microcapsule is solidified again, and the original color may be returned as the two color-forming substances are bonded.

Moreover, the camera 120 according to an exemplary embodiment may be configured to acquire image data of the user's surroundings. The image data may include image data for another party conversing or in communication with the user, i.e., the object. The camera 120 may include a plurality of lenses and an image sensor. The image sensor may include a plurality of photodiodes for converting light into electrical signals, and the plurality of photodiodes may be arranged in a two-dimensional matrix.

In addition, the camera 120 may be provided on the main body in which the controller 130 is provided, or may be provided on a separate wearable device. The camera 120 may be configured to perform wireless communication or wired communication through the controller 130 and the communication module, and the image data obtained through the camera 120 may be transmitted to the controller 130. The controller 130 may be configured to determine the emotion of the user based on the bio-signals obtained from the bio-signal sensor 112 and operate the display unit 113 to display the at least one of the colors and the patterns that correspond to the determined emotion.

As described above, the controller 130 may include the processor 131 for collecting and processing information received from the skin-attachment apparatus 110 and the memory 132 for storing various information and processing results required for the processing of the processor 131. The processor 131 according to the exemplary embodiment may be configured to determine the user's emotion based on the bio-signals obtained from the bio-signal sensor 112. The configuration for determining the user's emotion based on the biological signals will be described later in detail.

The processor 131 may be configured to operate the display unit 113 to display at least one of the color and the pattern corresponding to the determined emotion. Accordingly, the memory 132 may be configured to store information about the color and the pattern corresponding to the emotion, and the information may be set at a design stage. For example, the information on the color and the pattern corresponding to the emotion may include information that indicates that each of the colors and each of the patterns correspond to a blue color and a rainfall pattern.

As described above, the display unit 113 may include the plurality of LEDs. In particular, the display unit 113 may be configured to output at least one of the colors and the patterns corresponding to the determined emotion by operating each of the plurality of LEDs based on the control signal of the processor 131. In addition, as described above, the display unit 113 may include the insulating layer 113-1, the heat generating circuit 113-2, and the thermochromic pigment layer 113-3.

Particularly, the processor 131 may be configured to determine the color corresponding to the determined emotion, and operate the heat generating circuit 113-2 to generate heat at a temperature that corresponds to the determined color. This allows the thermochromic pigment layer 113-3 on the heat generating circuit 113-2 to change to the determined color to thus display the determined color on the display unit 113. Further, the processor 131 may be configured to determine the pattern that corresponds to the determined emotion, and operate the heat generating circuit 113-2 to generate heat in a region corresponding to the determined pattern. Thus, the determined pattern may be displayed on the display unit 113 by changing the color of the thermochromic pigment layer 113-3 on the heat generating circuit 113-2 only in the region corresponding to the determined pattern.

Further, the pattern that corresponds to the determined emotion may correspond to the facial expression corresponding to the determined emotion, according to the exemplary embodiment. In other words, the processor 131 may be configured to determine the facial expression that corresponds to the determined emotion, determine the pattern for each of the body parts based on the feature of the body part in the determined facial expression, and operate the display unit 113 to display the pattern corresponding to the body part to which the skin-attachment apparatus 110 is attached.

Specifically, the processor 131 may be configured to determine the facial expression in the emotion based on the determined emotion. Additionally, the processor 131 may use the information about the correlation between the emotion and the facial expression stored in the memory 132. Thereafter, the processor 131 may be configured to determine the feature of the body part (e.g., mouth, eye, eyebrow, eyebrow, forehead, nose, chin, etc.) in the facial expression determined based on the facial action coding system (FACS), and determine the pattern for each of the body parts to show the features of the body part.

For example, in response to determining that the user's emotion corresponds to an emotion corresponding to depression, the processor 131 may be configured to determine that the facial expression corresponding to the determined emotion corresponds to a depressed facial expression (e.g., sad facial expression), and determine the pattern for each of the body parts (e.g., pattern in which the shape of the mouth is going down) based on the features of the body part in the determined depressed facial expression (e.g., lowered mouth).

Thereafter, the processor 131 may be configured to operate the display unit 113 to display the pattern that corresponds to the body part, to which the skin-attachment apparatus 110 is attached, of the patterns for each of the body parts. For example, the processor 131 may be configured to operate the display unit 113 to display a pattern that corresponds to a mouth-tail among the patterns for each of the body parts, when the skin-attachment apparatus 110 is attached to the periphery of the mouth-tail.

Depending on the embodiment, the skin-attachment apparatus 110 may be provided in a plurality and may be attached to various locations of the user's body. In particular, each of the skin-attachment apparatuses 110 may communicate with the controller 130 to transmit and receive data. The processor 131 may be configured to operate the display unit 113 of each of the skin-attachment apparatuses 110 to display the pattern that corresponds to the body part to which each of the skin-attachment apparatuses 110 is attached out of the patterns for each of the body parts.

In addition, the controller 130 may be configured to determine the emotion of the object based on the image data of the object obtained through the camera 120, determine the feedback emotion corresponding to the determined emotion, and operate the skin-attachment apparatus 110 to display at least one of the color and the pattern corresponding to the determined feedback emotion. At this time, the object may correspond to the other party that is in communication with the user of the electronic device 10.

Particularly, the processor 131 may be configured to determine at least one of the facial expression and the behavior of the object based on the image data of the object included in the image data, and determine the emotion of the object based on at least one of the determined facial expression and the behavior. The processor 131 may use at least one of the correlation information between the facial expression and the emotion factor and the correlation information between the behavior and the emotion factor stored in the memory 132.

Thereafter, the processor 131 may be configured to determine the feedback emotion corresponding to the emotion of the object. The feedback emotion may correspond to an emotion generally felt by a person in response to the emotion of the other party, and may correspond to emotions that should be expressed for smooth conversation. For example, the feedback emotion may correspond to apologetic feelings when the emotions of the other party correspond to anger, and may correspond to emotions of emotional pleasure when the emotions of the other party correspond to happiness.

Thus, the electronic device 10 may be configured to determine the feedback feeling based on the feelings of a conversation partner and provide a corresponding image, thereby inducing an improved conversation with the conversation partner. For example, when a disabled person, a child, or the like who has difficulty expressing emotions uses the electronic device 10, the conversation partner may communicate with the user of the electronic device 10 while feeling more empathy. Accordingly, the processor 131 may utilize information about the feedback emotion according to the emotion stored in the memory 132. In particular, the processor 131 may be configured to determine the corresponding feedback emotion based on the determined emotion of the object.

In addition, the processor 131 may be configured to determine the feedback emotion using the neural network. Specifically, the processor 131 may be configured to perform an arithmetic operation on the emotion of the object using the neural network, and determine the feedback emotion corresponding to the emotion of the object based on the information on the arithmetic operation using the neural network. The information according to the operation using the neural network may include information about the feedback emotion corresponding to the emotion of the object.

Since the above-described neural network refers to machine learning that forms a neural structure capable of performing deep learning, the weight and bias corresponding to the configuration of the neural network are continuously changed to improve the reliability of learning. Specifically, the electronic device 10 may be configured to continuously update a weight, a bias, and an activation function included in the neural network based on the information about the change in the emotion of the object according to the feedback emotion and the emotion change, and thus the inference result of the neural network may be improved.

In other words, the processor 131 may be configured to determine the emotion change of the object with respect to at least one of the color and the pattern corresponding to the feedback emotion determined based on the image data of the object, and the neural network may be updated based on the determined feedback emotion and the emotion change of the object. In other words, the electronic device 10 may be configured to store information on the emotion change of the object according to the determined feedback emotion and emotion change when the feedback emotion is determined, and may be configured to update the stored neural network continuously based on the stored feedback emotion and the information of the emotion change of the object.

On the other hand, the neural network may be transmitted to the electronic device 10 in a learned state based on a plurality of feedback emotions and information on the emotion change of the object according to each of the feedback emotions, and the electronic device 10 may be configured to receive information on the emotion change of the object in accordance with the plurality of feedback emotions and each of the feedback emotions from an external server and learn the neural network based on the received information. The neural network may be stored in the memory 132 in the form of a computer program. Hereinafter, the computation performed by the neural network in a coding form of the computer program will be described. However, the present disclosure is not limited to the computer program in which the neural network is stored.

Particularly, the neural network may be configured to generate a feature map output by convoluting information on the emotion change of the object according to the feedback emotion and emotion change, and output the feature map to the neural network using a convolution neural network, but it is not limited thereto, and may be performed by another deep-learning algorithm including recurrent neural networks (RNN). Thereafter, the processor 131 according to one exemplary embodiment may be configured to operate the display unit 113 of the skin-attachment apparatus 110 to display at least one of the colors and the patterns corresponding to the determined feedback emotion. The processor 131 may use the information on the color and the pattern corresponding to the emotion stored in the memory 132, and in accordance with an exemplary embodiment, may be configured to display the pattern representing the facial expression in the corresponding emotion.

Accordingly, the controller 130 may include at least one of the memories 132 storing a program for performing the above-described operations and operations described later, and at least one of the processors 131 for executing the stored program. When there are a plurality of the memories 132 and the processor 131, they may be integrated in one chip or provided at physically separated positions. In addition, the memory 132 includes a non-volatile memory medium such as a cache, read only memory (ROM), programmable ROM (PROM), erasable programmable ROM (EPROM), electrically erasable programmable ROM (EEPROM), and a flash memory; a volatile memory medium such as random access memory (RAM); or a storage medium such as a hard disk drive (HDD), a CD-ROM, or the like, but is not limited thereto.

Figure 4:
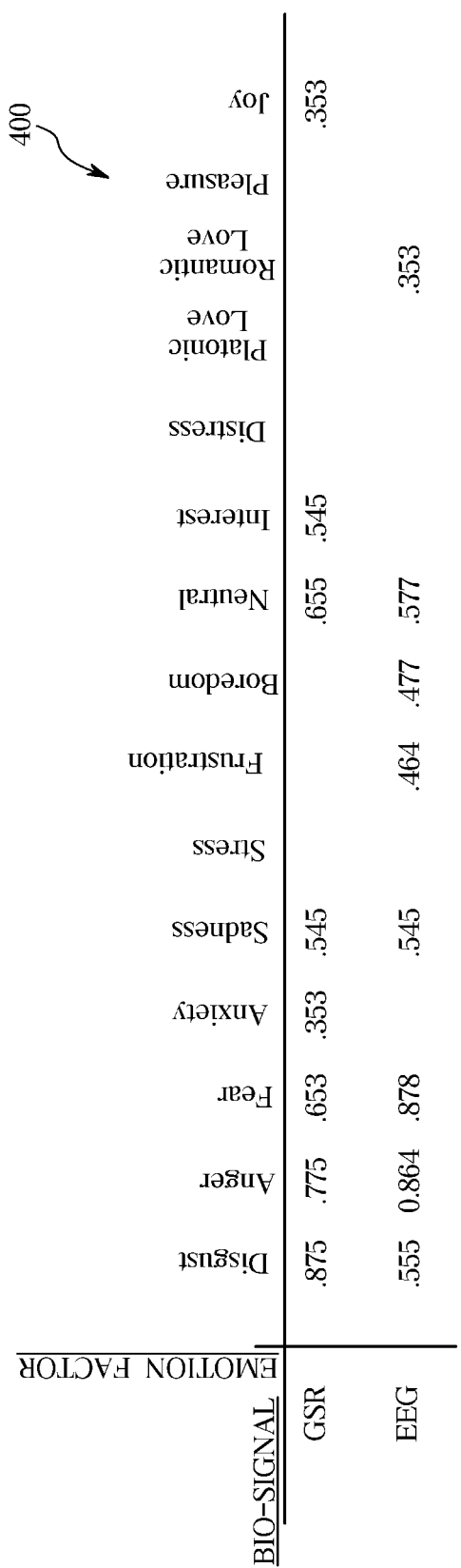
FIG. 4 is a diagram illustrating correlation information between a bio-signal and an emotion factor according to an exemplary embodiment.
Figure 5:
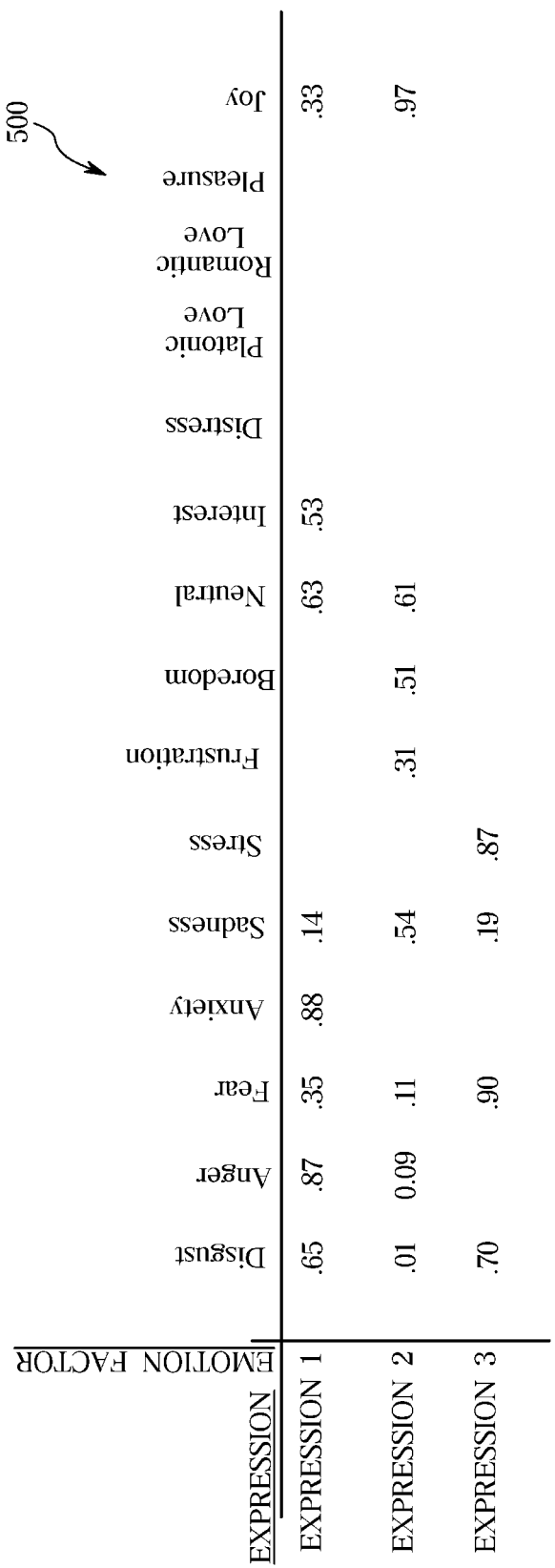
FIG. 5 is a diagram illustrating correlation information between a facial expression and an emotion factor according to an exemplary embodiment.
Figure 6:
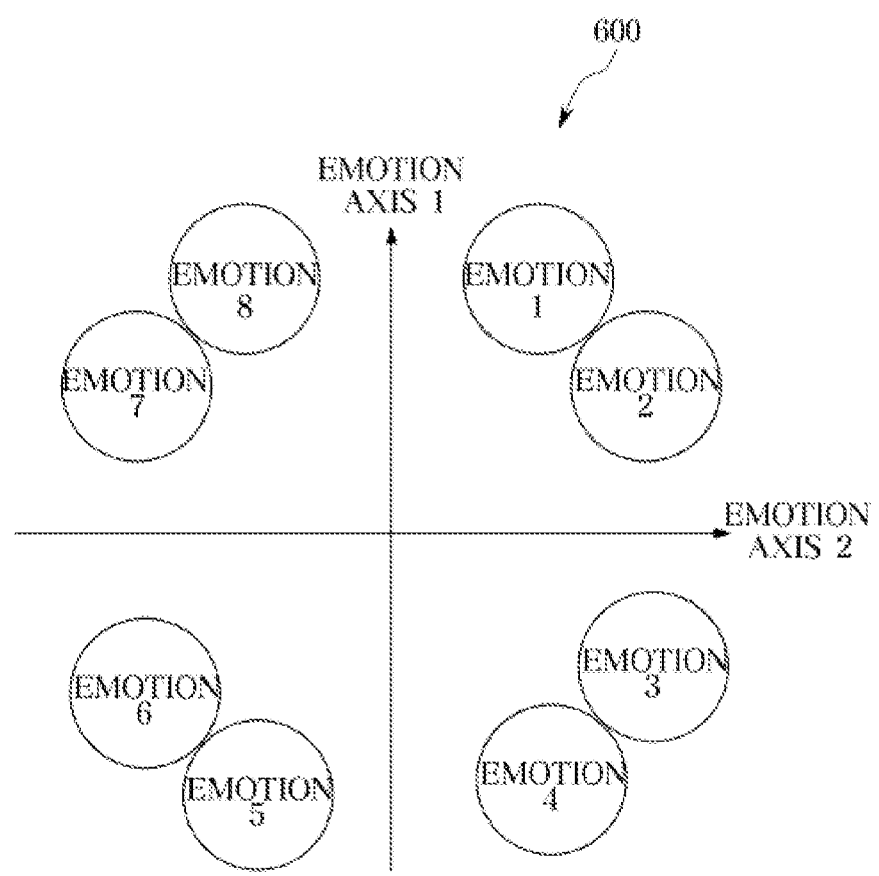
FIG. 6 is a diagram illustrating an emotion model according to an exemplary embodiment.

Hereinafter, reference will now be made in detail about the electronic device 10 determining the emotion of the user based on the bio-signals obtained from the bio-signal sensor 112 and the emotion of the object based on the image data of the object obtained from the camera 120. FIG. 4 is a diagram illustrating correlation information between a bio-signal and an emotion factor according to an exemplary embodiment, FIG. 5 is a diagram illustrating correlation information between a facial expression and an emotion factor according to an exemplary embodiment, and FIG. 6 is a diagram illustrating an emotion model according to an exemplary embodiment.

Referring to FIG. 4, correlation information 400 between the bio-signal and the emotion factor according to an exemplary embodiment may include correlation information between a galvanic skin response (GSR), an electroencephalogram (EEG) and an emotion factor. As shown in FIG. 4, a GSR signal has a correlation value of about 0.875 and 0.775 in disgust and anger emotional factors, respectively, and has a high correlation with the disgust or anger emotional factors. Therefore, the user's bio-signals collected by the GSR sensor are the base on which the user's emotions may be determined as anger or disgust.

In the case of a pleasant (happy) emotional factor, the correlation value with the GSR signal is relatively low (e.g., about 0.353), and thus, the pleasant emotional factor is less relevant to the GSR signal. An EEG signal has a correlation coefficient of about 0.864 and 0.878 with anger and fear emotional factors, respectively, which is more related to the anger and afraid emotional factors than other emotional factors. Therefore, the bio-signals collected by the EEG sensor are the base on which the user's feelings may be determined as the angry emotion or the fear emotion.

Accordingly, the processor 131 of the controller 130 may be configured to acquire information regarding the emotional state of each of the users by using the correlation information 400 between the bio-signal and the emotion factor. Since the information shown in FIG. 4 is merely an experiment result, it may be variously changed according to the experimental environment. In addition, FIG. 4 shows only the correlation information between the galvanic skin response (GSR), the electroencephalogram (EEG) and the emotion factor, and the correlation information 400 between the biological signal and the emotion factor may include the correlation information between each of the biological signals and the emotion factor according to the type of the bio-signals measured from the sensor provided in the electronic device 10.

Referring to FIG. 5, the controller 130 according to an exemplary embodiment may be configured to determine the facial expressions of the object represented by an image of a target object photographed by the camera 120, and obtain the emotion of the object by applying the facial action coding system (FACS) on the facial expression of the object. Specifically, the processor 131 of the controller 130 may be configured to extract the feature points from the face of the object, and extract a plurality of face elements using the extracted feature points. The plurality of face elements may include eyebrows, eyes, nose, mouth, and the like. The processor 131 may be configured to combine the patterns for each of the plurality of extracted face elements and compare the combined pattern with correlation information 500 between the facial expression stored in the memory 132 and the emotion factor. The correlation information 500 between the facial expression and the emotion factor corresponds to the information indicating the relationship between the facial expression and emotion.

The processor 131 may be configured to determine the facial expression that corresponds to the same pattern or the most similar pattern as the combined pattern of the object among the correlation information 500 between the facial expression and the emotion factor as the facial expression of the object. In addition, the processor 131 may be configured to acquire information regarding the emotion of the object by considering the correlation value of the correlation information 500 between the facial expression and the emotion factor for the facial expression of the determined object.

For example, when the determined facial expression of the object corresponds to Facial Expression 2 in the correlation information 500 between the facial expression and the emotion factor, the processor 131 may be configured to determine that the pleasant emotion having a highest correlation value corresponds to the emotion of the object. The correlation information 500 between the facial expression and the emotion factor shown in FIG. 5 shows Expression 1, Expression 2, and Expression 3, but may include any facial expression capable of classifying the emotion of the object.

The processor 131 may also be configured to acquire information regarding the emotion of the object based on the behavior of the determined object and the correlation value of the correlation information (not shown) between the behavior stored in the memory 132 and the emotion factor. Accordingly, the controller 130 may be configured to analyze the image data of the object photographed by the camera 120, determine at least one of the facial expression and the behavior of the object corresponding to the user's conversation partner, and determine the emotion of the object based on at least one of the determined facial expression and behavior.

Referring to FIG. 6, emotion model 600 classifies emotions of an object according to the emotion of the user and image data of the object, which are displayed according to the user's bio-signals, on a graph. The emotion model 600 classifies the emotions of the user or the object based on a preset emotion axis. The emotion axis may be determined based on the image data of the object or the emotion measured by the user's bio-signals. For example, emotion axis 1 may be a positive degree or a negative degree measurable by the user's voice, and emotion axis 2 may be an excitement degree or an activation degree measurable by the GSR or the EEG When the emotion of the user or the object has a high positive degree and a high excitement, the emotion may be classified as Emotion 1 or Emotion 2. Conversely, when the emotion of the user or the object has a negative degree, and a high excitement degree, the emotion may be classified as Emotion 3 or Emotion 4. This emotion model may be a Russell's emotion model. The Russell's emotion model is represented by a two-dimensional graph based on the x- and y-axes, and classifies emotions into 8 domains with happiness (0 degrees), excitement (45 degrees), arousal (90 degrees), pain (135 degrees)), depression (225 degrees), sleepiness (270 degrees), and relaxation (315 degrees). In addition, the 8 domains are divided into 28 emotions and classified into similar emotions belonging to the 8 domains.

As described above, the processor 131 may be configured to determine the emotion of the user or the object using the bio-signals of the user, the image data for the target, the correlation information 400 between the bio-signal and the emotion factor, the correlation information 500 between the facial expression and the emotion factor, and the emotion model 600. Hereinafter, the case where the electronic device 10 according to the exemplary embodiment operates the display unit 113 to display at least one of the colors and the patterns corresponding to the emotion based on the determined emotion of the user will be described in detail.

Figure 8:
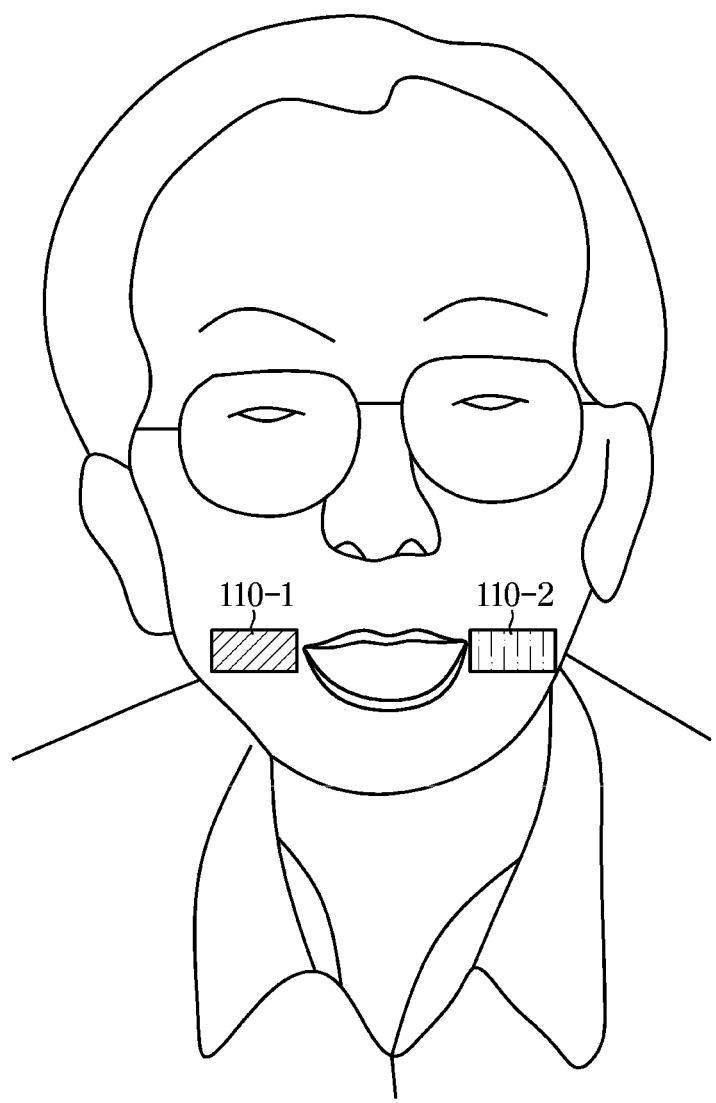
FIG. 8 is a diagram illustrating a case where an electronic device according to an exemplary embodiment displays at least one of a color and a pattern corresponding to a determined user's emotion.
Figure 9:
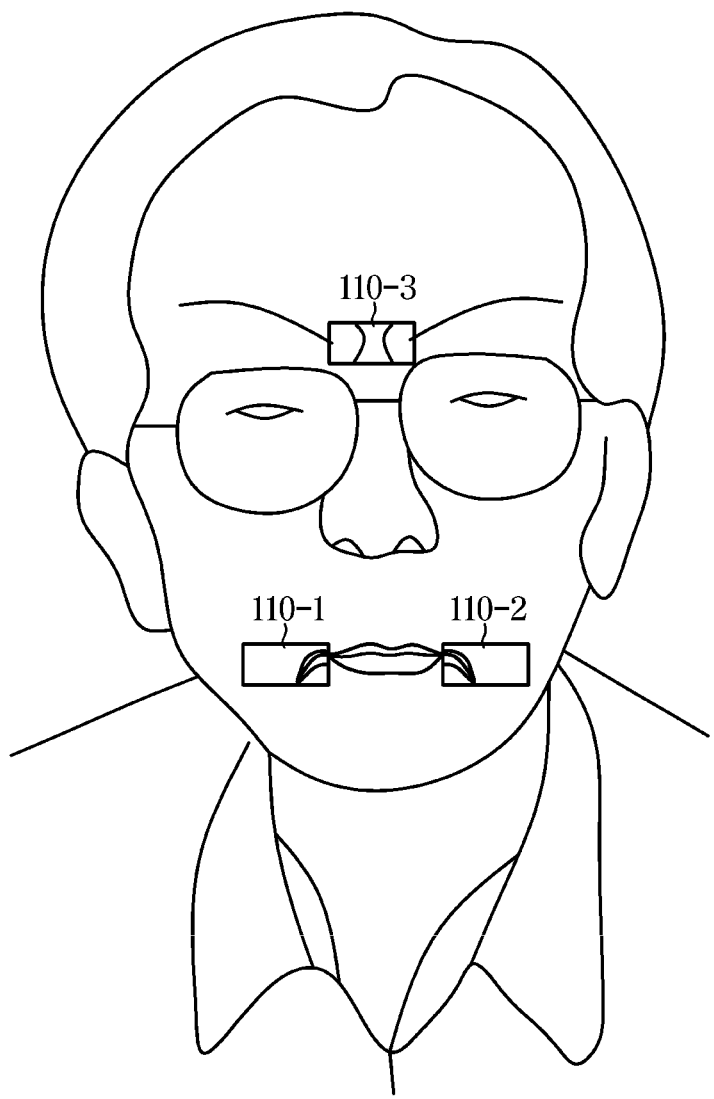
FIG. 9 is a diagram illustrating a case where an electronic device according to an exemplary embodiment displays a pattern corresponding to a facial expression in a determined user's emotion.

FIG. 7 is a diagram illustrating information on colors and patterns corresponding to an emotion according to an exemplary embodiment, FIG. 8 is a diagram illustrating a case where an electronic device according to an exemplary embodiment displays at least one of a color and a pattern corresponding to a determined user's emotion, and FIG. 9 is a diagram illustrating a case where an electronic device according to an exemplary embodiment displays a pattern corresponding to a facial expression in a determined user's emotion.

Referring to FIG. 7, the memory 132 according to one exemplary embodiment may include information regarding the colors and the patterns corresponding to emotions. The color and the pattern corresponding to the emotion may correspond to the color and the pattern representing the corresponding emotion. For example, the information regarding the color and the pattern corresponding to the emotion, as shown in FIG. 7, may include the information indicating that the color and the pattern representing the blue color and the rainfall corresponds to the emotion corresponding to depression, and the information indicating that the color and the pattern representing the pink color and the flower corresponds to the emotion corresponding to happiness.

However, the color and the pattern information corresponding to the emotion shown in FIG. 7 are merely an example, and information about the color and the pattern for each emotion that the user may feel may be included, and may be determined at the design stage of the electronic device 10. The processor 131 may be configured to operate the display unit 113 to display at least one of the color and the pattern corresponding to the emotion determined based on the information on the color and the pattern corresponding to this emotion.

In other words, the processor 131 may be configured to determine the emotion of the user based on the bio-signals measured through the bio-signal sensor 112, and operate the display unit 113 of the skin-attachment apparatus 110 to display at least one of the pattern and the color corresponding to determined emotion based on the information of the color and the pattern corresponding to the emotions. For example, the skin-attachment apparatus 110 may be provided in plurality as shown in FIG. 8, and under the operation of the processor 131, one skin-attachment apparatus 110-1 may be configured to display a color corresponding to the emotion and one skin-attachment apparatus 110-2 may be configured to display a pattern corresponding to the emotion (e.g., pattern shaped as rainfall).

As described above, the display unit 113 according to one exemplary embodiment may include the plurality of LEDs. In particular, the display unit 113 may be configured to output at least one of the colors and the patterns corresponding to the determined emotion by controlling each of the plurality of LEDs based on the control signal of the processor 131. In addition, as described above, the display unit 113 according to one exemplary embodiment may include the insulating layer 113-1, the heat generating circuit 113-2, and the thermochromic pigment layer 113-3.

Particularly, the processor 131 may be configured to determine the color corresponding to the determined emotion, and operate the heat generating circuit 113-2 to generate heat at a temperature corresponding to the determined color. This allows the thermochromic pigment layer 113-3 on the heat generating circuit 113-2 to change to the determined color to thus display the determined color on the display unit 113. Further, the processor 131 may be configured to determine the pattern corresponding to the determined emotion, and operate the heat generating circuit 113-2 to generate heat in a region corresponding to the determined pattern. Thus, the determined pattern may be displayed on the display unit 113 by changing the color of the thermochromic pigment layer 113-3 on the heat generating circuit 113-2 only in the region corresponding to the determined pattern.

Further, the pattern corresponding to the determined emotion may correspond to the facial expression corresponding to the determined emotion. Specifically, the information on the color and the pattern corresponding to the emotion includes information that indicates that the pattern corresponding to the emotion corresponding to the depression corresponds to the pattern showing the depressed facial expression, and information indicating that the pattern corresponding to the emotion corresponding to the happiness corresponds to the pattern showing the happy facial expression as shown in FIG. 7.

In other words, the processor 131 according to the exemplary embodiment may be configured to determine the facial expression corresponding to the determined emotion, determine the pattern for each of the body parts based on the feature of the body part in the determined facial expression, and operate the display unit 113 to display the determined pattern corresponding to the body part to which the skin-attachment apparatus 110 is attached. Specifically, the processor 131 may be configured to determine the facial expression in the emotion based on the determined emotion. The processor 131 may use the information about the correlation between the emotion and the facial expression stored in the memory 132.

The processor 131 may then be configured to determine the feature of the body part (e.g., mouth, eye, eyebrow, eyebrow, forehead, nose, chin, etc.) in the facial expression determined based on the facial action coding system (FACS), and determine the pattern for each of the body parts to show the features of the body parts. For example, in response to determining that the user's emotion corresponds to an emotion corresponding to depression, the processor 131 may be configured to determine that the facial expression corresponding to the determined emotion corresponds to a depressed facial expression (e.g., sad facial expression), and determine the pattern for each of the body parts (e.g., pattern in which the shape of the mouth is going down) based on the features of the body part in the determined depressed facial expression (e.g., lowered mouth).

Thereafter, the processor 131 may be configured to operate the display unit 113 to display the pattern among the patterns for each of the body parts corresponding to the body part to which the skin-attachment apparatus 110 is attached. For example, the processor 131 may be configured to operate the display unit 113 of the skin-attachment apparatus 110 to display a pattern corresponding to a mouth-tail among the patterns for each of the body parts, when the skin-attachment apparatus 110 is attached to the periphery of the mouth-tail.

Depending on the embodiment, the skin-attachment apparatus 110 may be provided in a plurality and may attached to various locations of the user's body. In particular, each of the skin-attachment apparatuses 110 may be configured to communicate with the controller 130 to transmit and receive data. The processor 131 may be configured to operate the display unit 113 of each of the skin-attachment apparatuses 110 to display the pattern corresponding to the body part to which each of the skin-attachment apparatuses 110 is attached out of the patterns for each of the body parts. For example, the skin-attachment apparatus 110 may be attached to the periphery of the left mouth-tail, the periphery of the right mouth-tail, and the eyebrows, respectively, as shown in FIG. 9. In particular, the processor 131, when the determined emotion corresponds to depression and the pattern for each of the body parts corresponding to the depressed facial expression is determined, as shown in FIG. 9, may be configured to operate the skin-attachment apparatus 110-1, 110-2 attached to the periphery of the mouth of the user to display a pattern that shapes of the mouth lowered, and operate a skin-attachment apparatus 110-3 attached between the eyebrows to display a pattern that depicts the shape of the frown.

As described above, the electronic device 10 may be configured to display the image (e.g., at least one of the color and the pattern) that corresponds to the emotion determined based on the bio-signals. This process may aid with the emotional expressions of users having difficulty in expressing their emotions (e.g., patients, the disabled, children, and elderly people), and facilitate improved understanding between the communication partner and the user's emotions. Further, the electronic device 10 may be used to determine the accuracy of the emotion determination based on the bio-signals by displaying the determined emotion as an image.

Hereinafter, the manner in which the electronic device 10 according to the exemplary embodiment determines the emotion of the object based on the image data of the object acquired through the camera 120 and determines the feedback emotion corresponding to the emotion of the object will be described in detail. FIG. 10 is a diagram illustrating information on a feedback emotion corresponding to an emotion of an object according to an exemplary embodiment.

Particularly, the controller 130 may be configured to determine the emotion of the object based on the image data of the object obtained through the camera 120, determine the feedback emotion corresponding to the determined emotion, and operate the skin-attachment apparatus 110 to display at least one of the color and the pattern corresponding to the determined feedback emotion. The object may correspond to the other party that is in communication with the user of the electronic device 10.

The processor 131 may be configured to determine at least one of the facial expression and the behavior of the object based on the image data of the object included in the image data, and determine the emotion of the object based on the at least one of the determined facial expression and the behavior. The processor 131 may use at least one of the correlation information 500 between the facial expression and the emotion factor stored in the memory 132 and the correlation information (not shown) between the behavior and the emotion factor. Thereafter, the processor 131 may be configured to determine the feedback emotion corresponding to the emotion of the object. The feedback emotion may correspond to an emotion generally experienced by the person in response to the emotion of the other party, and may correspond to emotions that should be expressed for improved communication.

Thus, the electronic device 10 may be configured to determine the feedback feeling based on the feelings of the conversation partner and provide a corresponding image, thereby inducing an improved conversation with the conversation partner. For example, when a disabled person, a child, or the like who has difficulty expressing emotions uses the electronic device 10, the conversation partner may communicate with the user of the electronic device 10 while feeling more empathy. Accordingly, the processor 131 may utilize information about the feedback emotion according to the emotion stored in the memory 132. As shown in FIG. 10, the information about the feedback emotion according to the emotion may include information that indicates that the feedback emotion corresponds to an apologetic emotion when the emotion of the other party corresponds to anger, and information that indicates that the feedback emotion corresponds to the emotion of pleasure due to empathy when the emotion of the other party corresponds to happiness.

However, the feedback information according to the emotion shown in FIG. 10, is merely an example, and the feedback emotion corresponding to the various emotions of the object may be set in the design stage and stored in the memory 132. In particular, the processor 131 may be configured to determine the corresponding feedback emotion based on the determined emotion of the object. In addition, the processor 131 may be configured to determine the feedback emotion using the neural network, according to an exemplary embodiment. Specifically, the processor 131 may be configured to perform an arithmetic operation on the emotion of the object using the neural network, and determine the feedback emotion corresponding to the emotion of the object based on the information on the arithmetic operation using the neural network. The information according to the operation using the neural network may include information about the feedback emotion corresponding to the emotion of the object.

Since the above-described neural network refers to machine learning that forms a neural structure capable of performing deep learning, the weight and bias corresponding to the configuration of the neural network may be continuously changed to improve the reliability of learning. Specifically, the electronic device 10 may be configured to continuously update a weight, a bias, and an activation function included in the neural network based on the information about the change in the emotion of the object according to the feedback emotion and the emotion change, and thus improves the inference result of the neural network.

In other words, the processor 131 may be configured to determine the emotion change of the object with respect to at least one of the color and the pattern corresponding to the feedback emotion determined based on the image data of the object, and update the neural network based on the determined feedback emotion and the emotion change of the object. In other words, the electronic device 10 may be configured to store information on the emotion change of the object according to the determined feedback emotion and the emotion change, when the feedback emotion is determined, and update the stored neural network continuously based on the stored feedback emotion and the information of the emotion change of the object.

On the other hand, the neural network may be transmitted to the electronic device 10 in a learned state based on a plurality of feedback emotions and information regarding the emotion change of the object according to each of the feedback emotions, and the electronic device 10 may be configured to receive information regarding the emotion change of the object in accordance with the plurality of feedback emotions and each of the feedback emotions from the external server and may learn the neural network based on the received information.

Furthermore, the neural network may be configured to generate a feature map output by convoluting information on the emotion change of the object according to the feedback emotion and the emotion change, and output the feature map to the neural network using a convolution neural network, but it is not limited thereto, and may be performed by another deep-learning algorithm including RNN. Thereafter, the processor 131 may be configured to operate the display unit 113 of the skin-attachment apparatus 110 to display at least one of the colors and the patterns corresponding to the determined feedback emotion. The processor 131 may use the information on the color and the pattern corresponding to the emotion stored in the memory 132, and in accordance with an exemplary embodiment, may be configured to display the pattern representing the facial expression in the corresponding emotion.

Hereinafter, an operation method of the electronic device 10 according to an exemplary embodiment will be described. The electronic device 10 according to the above-described exemplary embodiment may be applied to the operation method of the electronic device 10, which will be described later. Therefore, the contents described above with reference to FIGS. 1 to 10 are equally applicable to the operation method of the electronic device 10 according to the exemplary embodiment, without any particular mention.

Figure 11:
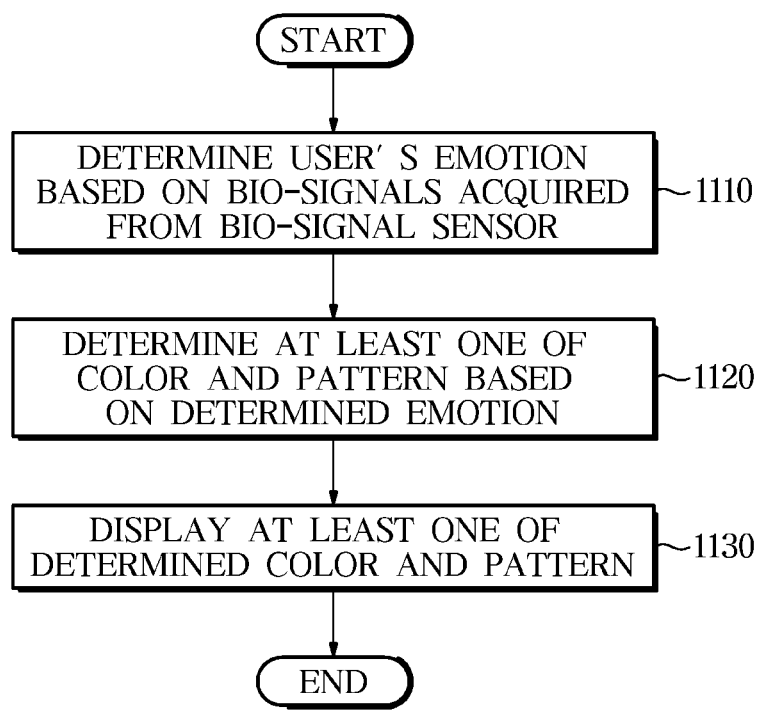
FIG. 11 is a flowchart showing a case of displaying an image corresponding to an emotion determined based on a bio-signal in a controlling method of an electronic device according to an exemplary embodiment.

FIG. 11 is a flowchart showing a case of displaying an image corresponding to an emotion determined based on a bio-signal in a controlling method of an electronic device according to an exemplary embodiment. Referring to FIG. 11, the electronic device 10 may be configured to determine the user's emotion based on bio-signals obtained from the bio-signal sensor 112 (1110). The determination of the emotion of the user based on the bio-signals is omitted in the same manner as described above.

Additionally, the electronic device 10 may be configured to determine at least one of a color and a pattern corresponding to the determined emotion (1120). The memory 132 may include information about the colors and the patterns corresponding to the emotions. The color and the pattern corresponding to the emotion may correspond to the color and the pattern representing the corresponding emotion. The processor 131 may be configured to determine at least one of the color and the pattern corresponding to the emotion determined based on the information on the color and the pattern corresponding to the emotion.

The electronic device 10 may be configured to display at least one of the determined colors and patterns (1130). In other words, the processor 131 may be configured to determine the user's emotion based on the bio-signals measured through the bio-signal sensor 112, and operate the display unit 113 of the skin-attachment apparatus 110 to display at least one of the color and the pattern corresponding to the determined emotion based on the information on the color and the pattern corresponding to the emotion.

As described above, the display unit 113 may include the plurality of LEDs. In particular, the display unit 113 may be configured to output at least one of the colors and the patterns corresponding to the determined emotion by controlling each of the plurality of LEDs based on the control signal of the processor 131. In addition, as described above, the display unit 113 according to one exemplary embodiment may include the insulating layer 113-1, the heat generating circuit 113-2, and the thermochromic pigment layer 113-3.

Particularly, the processor 131 may be configured to determine the color corresponding to the determined emotion, and operate the heat generating circuit 113-2 to generate heat at a temperature corresponding to the determined color. This allows the thermochromic pigment layer 113-3 on the heat generating circuit 113-2 to change to the determined color so that the determined color may be displayed on the display unit 113. Further, the processor 131 may be configured to determine the pattern corresponding to the determined emotion, and operate the heat generating circuit 113-2 to generate heat in a region corresponding to the determined pattern.

Thus, the determined pattern may be displayed on the display unit 113 by changing the color of the thermochromic pigment layer 113-3 on the heat generating circuit 113-2 only in the region corresponding to the determined pattern. Further, the pattern corresponding to the determined emotion may correspond to the facial expression corresponding to the determined emotion. In other words, the processor 131 may be configured to determine the facial expression corresponding to the determined emotion, determine the pattern for each of the body parts based on the feature of the body part in the determined facial expression, and operate the display unit 113 to display the pattern corresponding to the body part to which the skin-attachment apparatus 110 is attached.

Specifically, the processor 131 may be configured to determine the facial expression in the emotion based on the determined emotion. The processor 131 may use the information about the correlation between the emotion and the facial expression stored in the memory 132. Thereafter, the processor 131 may be configured to determine the feature of the body part (e.g., mouth, eye, eyebrow, eyebrow, forehead, nose, chin, etc.) in the facial expression determined based on the facial action coding system (FACS), and determine the pattern for each of the body parts to show the features of the body part. Thereafter, the processor 131 may be configured to operate the display unit 113 to display the pattern corresponding to the body part, to which the skin-attachment apparatus 110 is attached, of the patterns for each of the body parts.

Figure 12:
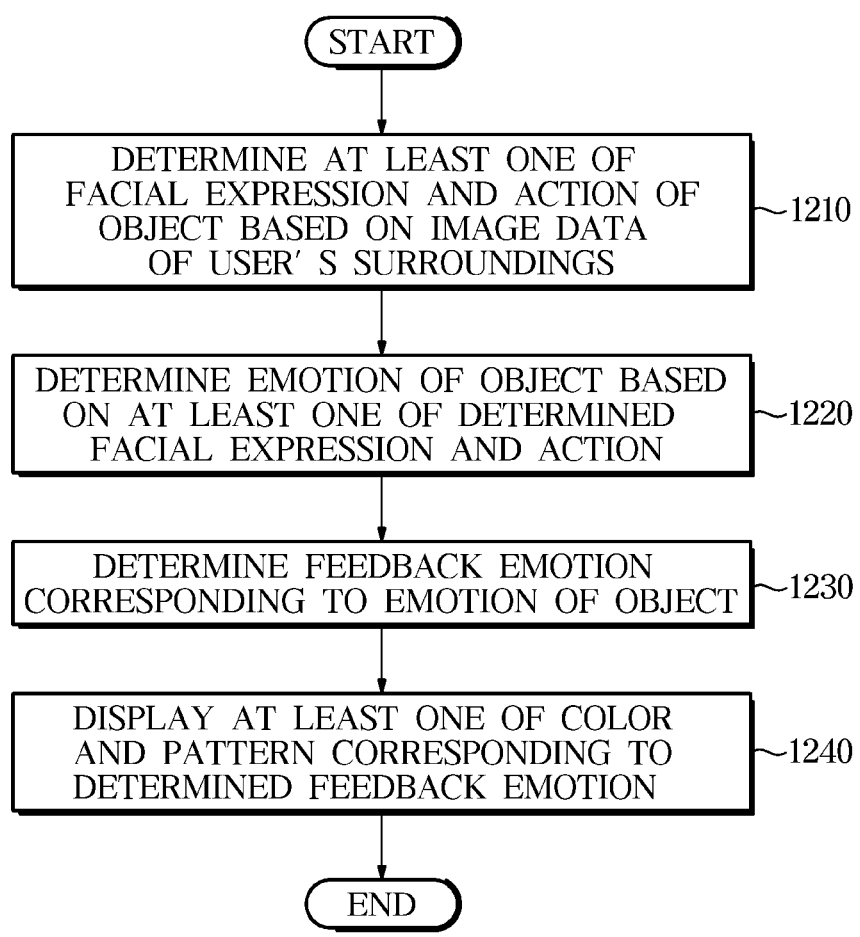
FIG. 12 is a flowchart showing a case in which an image corresponding to a feedback emotion is displayed based on an emotion of an object in a controlling method of an electronic device according to an exemplary embodiment.

FIG. 12 is a flowchart showing a case in which an image corresponding to a feedback emotion is displayed based on an emotion of an object in a controlling method of an electronic device according to an exemplary embodiment. Referring to FIG. 12, the electronic device 10 may be configured to determine (1210) at least one of a facial expression and a behavior of an object based on image data of the user's surroundings.

Specifically, the processor 131 may be configured to determine at least one of the facial expression and the behavior of the object based on the image data of the object included in the image data about the periphery of the user photographed through the camera 120. The object may correspond to the other party that is in communication with the user of the electronic device 10.

In addition, the electronic device 10 may be configured to determine the emotion of the object based on at least one of the determined facial expression and the behavior (1220). Specifically, the processor 131 may be configured to determine the emotion of the object based on at least one of the determined facial expression and behavior. The processor 131 may use at least one of the correlation information 500 between the facial expression and the emotion factor and the correlation information (not shown) between the behavior and the emotion factor stored in the memory 132.

Thereafter, the electronic device 10 may be configured to determine the feedback emotion corresponding to the emotion of the object (1230). In other words, the processor 131 may be configured to determine the feedback emotion corresponding to the emotion of the object. The feedback emotion may correspond to an emotion generally experienced by the person in response to the emotion of the other party, and may correspond to emotions that should be expressed for smooth conversation. Accordingly, the processor 131 may utilize information about the feedback emotion according to the emotion stored in the memory 132. In particular, the processor 131 may be configured to determine the corresponding feedback emotion based on the determined emotion of the object.

Additionally, the processor 131 may be configured to determine the feedback emotion using the neural network, according to an exemplary embodiment. Specifically, the processor 131 may be configured to perform an arithmetic operation on the emotion of the object using the neural network, and determine the feedback emotion corresponding to the emotion of the object based on the information on the arithmetic operation using the neural network. The information according to the operation using the neural network may include information about the feedback emotion corresponding to the emotion of the object.

Thereafter, the electronic device 10 may be configured to display at least one of the colors and the patterns corresponding to the determined feedback emotion (1240). In other words, the processor 131 may be configured to operate the display unit 113 of the skin-attachment apparatus 110 to display at least one of the colors and the patterns corresponding to the determined feedback emotion. The processor 131 may use the information on the color and the pattern corresponding to the emotion stored in the memory 132, and the pattern may represent the facial expression in the corresponding emotion.

Meanwhile, the disclosed exemplary embodiments may be embodied in the form of a recording medium storing instructions executable by a computer. The instructions may be stored in the form of a program code and, when executed by a processor, may generate a program module to perform the operations of the disclosed exemplary embodiments. The recording medium may be embodied as a non-transitory computer-readable recording medium. The non-transitory computer-readable recording medium includes all types of recording media in which instructions that can be decoded by a computer. For example, there may be read only memory (ROM), random access memory (RAM), a magnetic tape, a magnetic disk, a flash memory, an optical data storage device, and the like.

Although example exemplary embodiments of the disclosure have been shown and described, it would be appreciated by those skilled in the art that changes may be made to these exemplary embodiments without departing from the principles and spirit of the disclosure, the scope of which is defined in the claims and their equivalents.

REFERENCE NUMERAL LISTING

10: electronic device
110: skin-attachment apparatus
111: attachment unit
112: bio-signal sensor
113: display unit
120: camera
130: controller
131: processor
132: memory

What is claimed is:

1. An electronic device, comprising:
a skin-attachment apparatus configured to include a bonding unit for bonding to a user's skin, a bio-signal sensor configured to measure bio-signals of the user, and a display unit;
a memory configured to store at least one information of color information and pattern information corresponding to each of predetermined emotions; and
a processor configured to be connected with the skin-attachment apparatus, determine a user emotion based on the bio-signals acquired from the bio-signal sensor, and operate the display unit to display at least one of a color and a pattern corresponding to the determined emotion based on the at least one information,
wherein the display unit includes:
a heating circuit; and
a thermochromic pigment layer configured to include at least one thermochromic pigment provided on the heating circuit.

2. The electronic device of claim 1, wherein the processor is configured to determine the color corresponding to the determined emotion, and operate the heating circuit to generate heat at a temperature corresponding to the determined color.

3. The electronic device of claim 1, wherein the processor is configured to determine the pattern corresponding to the determined emotion, and operate the heating circuit to generate heat at a region of the heating circuit corresponding to the determined pattern.

4. The electronic device of claim 1, wherein the processor is configured to determine a facial expression corresponding to the determined emotion, determine a pattern for each body part based on a feature of the body part in the determined facial expression, and operate the display unit to display the pattern among the determined patterns corresponding to the body part to which the skin-attachment apparatus is attached.

5. The electronic device of claim 4, wherein the skin-attachment apparatus, respectively provided in plural, are attached to the different body parts.

6. The electronic device of claim 1, wherein the electronic device further includes:
a camera configured to acquire image data of user surroundings.

7. The electronic device of claim 6, wherein the processor is configured to determine at least one of a facial expression and an action of an object based on image data of the object included in the image data and determine an emotion of the object based on at least one of the determined facial expression and the action.

8. The electronic device of claim 7, wherein the processor is configured to determine a feedback emotion corresponding to the emotion of the object, and operate the display unit to display at least one of the color and the pattern corresponding to the determined feedback emotion.

9. The electronic device of claim 8, wherein the processor is configured to perform an arithmetic operation on the emotion of the object using a neural network, determine the feedback emotion corresponding to the emotion of the object based on the information on the operation performed using the neural network, determine a change in the emotion of the object with respect to at least one of the color and the pattern corresponding to the determined feedback emotion based on the image data of the object, and update the neural network based on the determined feedback emotion and the emotion change of the object.

10. A controlling method of an electronic device including a skin-attachment apparatus bonded to a user's skin, a bio-signal sensor configured to measure bio-signals of the user, and a display unit, the method comprising:
determining, by a processor, a user emotion based on the bio-signals acquired from the bio-signal sensor; and
operating, by the processor, the display unit to display at least one of a color and a pattern corresponding to the determined emotion based on stored at least one information of color information and pattern information corresponding to each of predetermined emotions, wherein the display unit includes:

a heating circuit; and a thermochromic pigment layer configured to include at least one thermochromic pigment provided on the heating circuit.

11. The method of claim 10, wherein the operating of the display unit includes:

determining, by the processor, the color corresponding to the determined emotion; and operating, by the processor, the heating circuit to generate heat at a temperature corresponding to the determined color.

12. The method of claim 10, wherein the operating of the display unit includes:

determining, by the processor, the pattern corresponding to the determined emotion; and operating, by the processor, the heating circuit to generate heat at a region of the heating circuit corresponding to the determined pattern.

13. The method of claim 10, wherein the operating of the display unit includes:

determining, by the processor, a facial expression corresponding to the determined emotion;

determining, by the processor, the pattern for each body part based on a feature of the body part in the determined facial expression; and operating, by the processor, the display unit to display the pattern among the determined patterns corresponding to the body part to which the skin-attachment apparatus is attached.

14. The method of claim 13, wherein the skin-attachment apparatus, respectively provided in plural, are attached to different body parts.

15. The method of claim 10, wherein the electronic device further includes:

a camera configured to acquire image data of user surroundings.

16. The method of claim 15, further comprising:

determining, by the processor, at least one of a facial expression and an action of an object based on image data of the object included in the image data; and determining, by the processor, an emotion of the object based on at least one of the determined facial expression and the action.

17. The method of claim 16, further comprising:

determining, by the processor, a feedback emotion corresponding to the emotion of the object;

operating, by the processor, the display unit to display at least one of the color and the pattern corresponding to the determined feedback emotion.

18. The method of claim 17, wherein the determining of the feedback emotion includes:

performing, by the processor, an arithmetic operation on the emotion of the object using a neural network;

determining, by the processor, the feedback emotion corresponding to the emotion of the object based on the information on the operation performed using the neural network;

determining, by the processor, a change in the emotion of the object with respect to at least one of the color and the pattern corresponding to the determined feedback emotion based on the image data of the object; and updating, by the processor, the neural network based on the determined feedback emotion and the emotion change of the object.

* * * * *